US012714789B2

(12) United States Patent
Johnson et al.

(10) Patent No.: US 12,714,789 B2
(45) Date of Patent: Aug. 25, 2026

(54) MEDICATION DELIVERY DEVICE INCLUDING DISPOSABLE AND REUSABLE PORTIONS

(71) Applicant: Eli Lilly and Company, Indianapolis, IN (US)

(72) Inventors: Caroline Grace Pyne Johnson, Carmel, IN (US); Adam Nathaniel Wiesler, Zionsville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 726 days.

(21) Appl. No.: 18/041,716

(22) PCT Filed: Aug. 23, 2021

(86) PCT No.: PCT/US2021/047082
§ 371 (c)(1),
(2) Date: Feb. 15, 2023

(87) PCT Pub. No.: WO2022/046600
PCT Pub. Date: Mar. 3, 2022

(65) Prior Publication Data

US 2023/0293818 A1 Sep. 21, 2023

Related U.S. Application Data

(60) Provisional application No. 63/070,570, filed on Aug. 26, 2020.

(51) Int. Cl.
*A61M 5/24* (2006.01)
*A61M 5/20* (2006.01)
(Continued)

(52) U.S. Cl.
CPC ............ *A61M 5/20* (2013.01); *A61M 5/2422* (2013.01); *A61M 5/31515* (2013.01);
(Continued)

(58) Field of Classification Search
CPC .. A61M 5/20; A61M 5/2422; A61M 5/31515; A61M 5/46; A61M 2005/206;
(Continued)

(56) References Cited

U.S. PATENT DOCUMENTS 5,865,805 A 2/1999 Ziemba et al.
6,302,869 B1 10/2001 Klitgaard
(Continued)

FOREIGN PATENT DOCUMENTS

KR 200480998 Y1 8/2016
WO 2017174668 10/2017
(Continued)

OTHER PUBLICATIONS

Patent Cooperation Treaty International Search Report of the International Searching Authority pertaining to International Application No. PCT/US2021/047082; International Filing Date: Aug. 23, 2021; Date of Mailing: Nov. 29, 2021.
(Continued)

*Primary Examiner* — Tasnim Mehjabin Ahmed
(74) *Attorney, Agent, or Firm* — M. Daniel Spillman

(57) ABSTRACT

A medication delivery device including a disposable portion and a reusable portion. The disposable portion can include a carrier and a syringe coupled with the carrier. The reusable portion can include a housing which includes radial opening that can receive the disposable portion in a radial direction. The reusable portion also includes a shuttle that includes a guide that can receive the carrier of the disposable portion through the radial opening. The reusable portion also includes an actuator assembly coupled with the shuttle that can move the disposable portion through the passageway of the housing between a stowed state in which the needle is concealed within the housing, a deployed state in which the needle extends from the housing to deliver the medication to
(Continued)

a patient, and a retracted state in which the needle is retracted into the housing.

26 Claims, 13 Drawing Sheets

(51) Int. Cl.
*A61M 5/315* (2006.01)
*A61M 5/46* (2006.01)

(52) U.S. Cl.
CPC ......... *A61M 5/46* (2013.01); *A61M 2005/206* (2013.01); *A61M 2005/2073* (2013.01); *A61M 2005/2414* (2013.01); *A61M 2005/2485* (2013.01); *A61M 2005/2492* (2013.01); *A61M 2005/31588* (2013.01); *A61M 2205/50* (2013.01); *A61M 2205/502* (2013.01); *A61M 2205/8206* (2013.01)

(58) Field of Classification Search
CPC .. A61M 2005/2073; A61M 2005/2414; A61M 2005/2485; A61M 2005/2492; A61M 2005/31588; A61M 2205/50; A61M 2205/502; A61M 2205/8206
See application file for complete search history.

(56) References Cited

U.S. PATENT DOCUMENTS

| | | | | |
|---|---|---|---|---|
| 7,220,248 | B2 * | 5/2007 | Mernoe | A61M 5/14244 604/218 |
| 8,177,749 | B2 | 5/2012 | Slate et al. | |
| 8,376,993 | B2 | 2/2013 | Cox et al. | |
| 8,920,374 | B2 | 12/2014 | Bokelman et al. | |
| 9,061,103 | B2 | 6/2015 | Kemp et al. | |
| 9,192,731 | B2 | 11/2015 | Roberts et al. | |
| 9,289,556 | B2 | 3/2016 | Manke et al. | |
| 10,092,706 | B2 | 10/2018 | Denzer et al. | |
| 10,137,258 | B2 | 11/2018 | Mukai et al. | |
| 10,173,012 | B2 | 1/2019 | Dasbach | |
| 10,492,990 | B2 | 12/2019 | Mounce et al. | |
| 2003/0105430 | A1 | 6/2003 | Lavi et al. | |
| 2011/0172602 | A1 * | 7/2011 | Eaton | A61M 5/3243 604/134 |
| 2011/0224616 | A1 | 9/2011 | Slate et al. | |
| 2013/0281936 | A1 | 10/2013 | Kemp et al. | |
| 2016/0120751 | A1 * | 5/2016 | Mounce | A61P 19/10 604/404 |
| 2016/0354556 | A1 | 12/2016 | Zucker et al. | |
| 2019/0015591 | A1 | 1/2019 | Morlock et al. | |
| 2019/0328973 | A1 | 10/2019 | Cowe et al. | |
| 2019/0351139 | A1 | 11/2019 | Sarkorov et al. | |
| 2019/0381240 | A1 | 12/2019 | Novickoff et al. | |

FOREIGN PATENT DOCUMENTS

| | | |
|---|---|---|
| WO | 2019118261 | 6/2019 |
| WO | 2019191104 | 10/2019 |

OTHER PUBLICATIONS

Patent Cooperation Treaty Written Opinion of the International Searching Authority pertaining to International Application No. PCT/US2021/047082; International Filing Date: Aug. 23, 2021; Date of Mailing: Nov. 29, 2021.

* cited by examiner

MEDICATION DELIVERY DEVICE INCLUDING DISPOSABLE AND REUSABLE PORTIONS

BACKGROUND

The present disclosure pertains to medication delivery devices, and, in particular, to a portable medication delivery device such as an injector pen.

Patients suffering from a number of different diseases frequently must inject themselves with medication. To allow a person to conveniently and accurately self-administer medicine, a variety of devices broadly known as injector pens or injection pens have been developed. Generally, these pens are equipped with a cartridge including a piston and one or more doses of liquid medication. A drive member, extending from within a base of the injector pen and operably connected with typically more rearward mechanisms of the pen that control drive member motion, is movable forward to advance the piston in the cartridge in such a manner to dispense the contained medication from an outlet at the opposite cartridge end, typically through a needle that penetrates a stopper at that opposite end. In disposable pens, after a pen has been used and exhausted the supply of medication within the cartridge, the entire pen is discarded by a user, who may then begin using a replacement pen. In reusable pens, after a pen has been used and exhausted the supply of medication within the cartridge, the pen is disassembled, the spent cartridge is replaced with a fresh cartridge, and the pen is reassembled for its subsequent use.

It would be desirable to provide a medication delivery device with improved features, such as a providing a reusable device that facilitates ease of replacement of a spent cartridge with a fresh cartridge and reduces the size and/or the number of components of the spent cartridge to reduce waste.

SUMMARY

According to an embodiment of the present disclosure, a medication delivery device is provided. The medication delivery device includes a disposable portion and a reusable portion. The disposable portion includes a carrier and a syringe coupled with the carrier. The syringe includes a barrel to contain a medication, a piston positioned within the barrel, and a needle positioned at a distal end of the barrel. The reusable portion includes a housing, shuttle, and an actuator assembly. The housing includes a passageway extending along a longitudinal axis between a proximal end and a distal end of the housing. The disposable portion can be removably positioned within the passageway. The housing also includes a radial opening that is configured to receive the disposable portion in a radial direction. The shuttle includes a guide that is configured to receive the carrier of the disposable portion through the radial opening. The actuator assembly is coupled with the shuttle, The actuator assembly is also configured to move the disposable portion through the passageway of the housing between a stowed state in which the needle is concealed within the distal end of the housing, a deployed state in which the needle extends from the distal end of the housing to deliver the medication to a patient, and a retracted state in which the needle is retracted into the distal end of the housing.

According to another embodiment of the present disclosure, a method of operating a medication delivery device is provided. The method includes obtaining a disposable syringe containing a medication and inserting the disposable syringe in a radial direction through a radial opening in a reusable housing. The method also includes actuating the medication delivery device to move the disposable syringe through the reusable housing in a longitudinal direction perpendicular to the radial direction and into a patient's skin and to deliver the medication into the patient's skin. The method also includes retracting the disposable syringe into the reusable housing in the longitudinal direction, and removing the disposable syringe from the reusable housing.

In yet another embodiment of the present disclosure, a method of delivering a medication with a medication delivery device is provided. The medication delivery device includes a reusable portion and a disposable portion where the disposable portion contains the medication. The method includes receiving a command to activate the medication delivery device. The method also includes inserting the disposable portion into a housing of the reusable portion through a radial opening in the housing where a carrier of the disposable portion couples with a guide of a shuttle of the reusable portion. The method also includes receiving a command to remove a shield from a needle of the disposable portion. The command causes can actuator to advance the guide to a first axial position within the housing where the shield contacts a set of fingers in the housing. The command also causes the actuator to retract the shuttle causing the shield to decouple from the needle. The method also includes pressing a user input to cause the actuator to advance the guide to a second axial position within the housing to expose the needle from a distal end of the housing and deliver the medication from the disposable portion. The method also includes automatically retracting the actuator to retreat the guide to a third axial position within the housing after the pressing step. The method also includes receiving a command to dispose of the reusable portion. This command causes the actuator to advance the guide to a fourth axial position within the housing where the guide releases the carrier.

In yet another embodiment of the present disclosure, a method of delivering a medication with a medication delivery device is provided. The medication delivery device includes a reusable portion and a disposable portion where the disposable portion contains the medication. The method includes inserting a disposable portion into a housing of the reusable portion through a radial opening in the housing wherein a carrier of the disposable portion couples with a guide of a shuttle of the reusable portion. The method also includes rotating a locking mechanism causing the shuttle to advance the disposable portion to a first axial position within the housing where a shield on a needle of the disposable portion is coupled with a basecap. The method also includes separating the medication delivery device from the basecap wherein the shield is decoupled from the needle. The method also includes pressing a user input for a first time causing the shuttle to advance the disposable portion to a second axial position within the housing to expose the needle from a distal end of the housing and deliver the medication. The method also includes pressing the user input for a second time causing the shuttle to retract the disposable portion to a third axial position within the housing. The method also includes replacing the medication delivery device on the basecap to recouple the shield and the needle. The method also includes removing the disposable portion from the reusable portion in a radial direction through the opening in the housing, wherein the carrier decouples from the guide.

BRIEF DESCRIPTION OF THE DRAWINGS

The above-mentioned and other advantages and objects of this invention, and the manner of attaining them, will become more apparent, and the invention itself will be better understood, by reference to the following description of embodiments of the invention taken in conjunction with the accompanying drawings, wherein.

Figure 1:
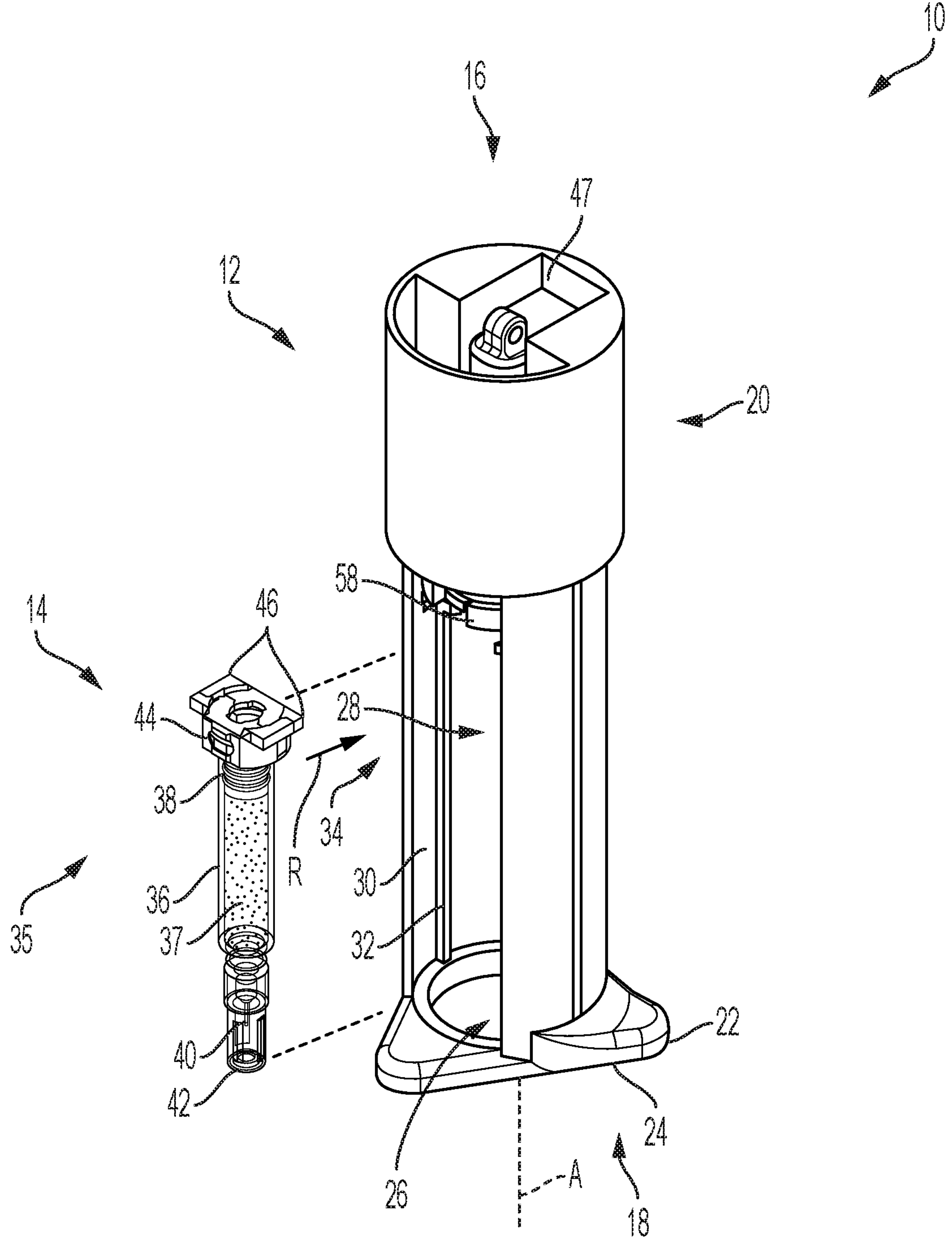
FIG. 1 is a perspective view of a medication delivery device according to embodiments of the present disclosure.

Corresponding reference characters indicate corresponding parts throughout the several views. Although the drawings represent embodiments of the present invention, the drawings are not necessarily to scale, and certain features may be exaggerated or omitted in some of the drawings in order to better illustrate and explain the present invention.

DETAILED DESCRIPTION

Medication delivery devices according to the present disclosure carry and dispense one or more medications, which may also be referred to as medications or drugs. Medication delivery devices according to the present disclosure are operated in a manner generally as described herein by a user (for example, a healthcare professional, a caregiver, or another person) to deliver one or more medications to a patient (for example, another person or the user).

Any directional references used with respect to any of the Figures, such as right or left, up or down, or top or bottom, are intended for convenience of description, and does not limit the present disclosure or any of its components to any particular positional or spatial orientation.

By way of illustration, the medication delivery device is described in the form of an autoinjector. However, the medication delivery device may be any device which is used to set and to deliver a dose of a medication, such as pen injectors, infusion pumps and syringes. The medication may be any of a type that may be delivered by such a medication delivery device. The device may be configured for a single fixed dose injection or a series of fixed dosage injections. Other embodiments of devices could be configured for a series of variable doses. The device may include a disposable device after the exhaustion of the medication or a reusable device capable of receiving a new cartridge of medication after exhaustion of the used cartridge of medication.

In one embodiment, the medication delivery device may provide a novel side loading capability for a disposable syringe assembly into a reusable assembly that is configured to receive the syringe assembly. In one embodiment, the medication delivery device may provide a reusable assembly having a novel coupling mechanism configured to receive a novel coupling mechanism of a syringe assembly. In one embodiment, the medication delivery device may provide a reusable assembly having a novel coupling mechanism that when coupled to a novel coupling mechanism of a syringe assembly that allows a first drive mechanism to extend the syringe and/or retract the syringe after its extension, and allows a second drive to extend a plunger for driving piston distally to expel the medication and/or to retract the plunger to allow for engagement with a piston of a new syringe. In one embodiment, one or more syringe assembly with the same or different medications with the same or different dosages (for different treatments and/or titration) with the novel coupling mechanism as described may be distributed separately from that of the reusable portion. In one embodiment, a reusable portion with the novel coupling mechanism as described may be distributed separately from that of the syringe assembly.

Figure 2:
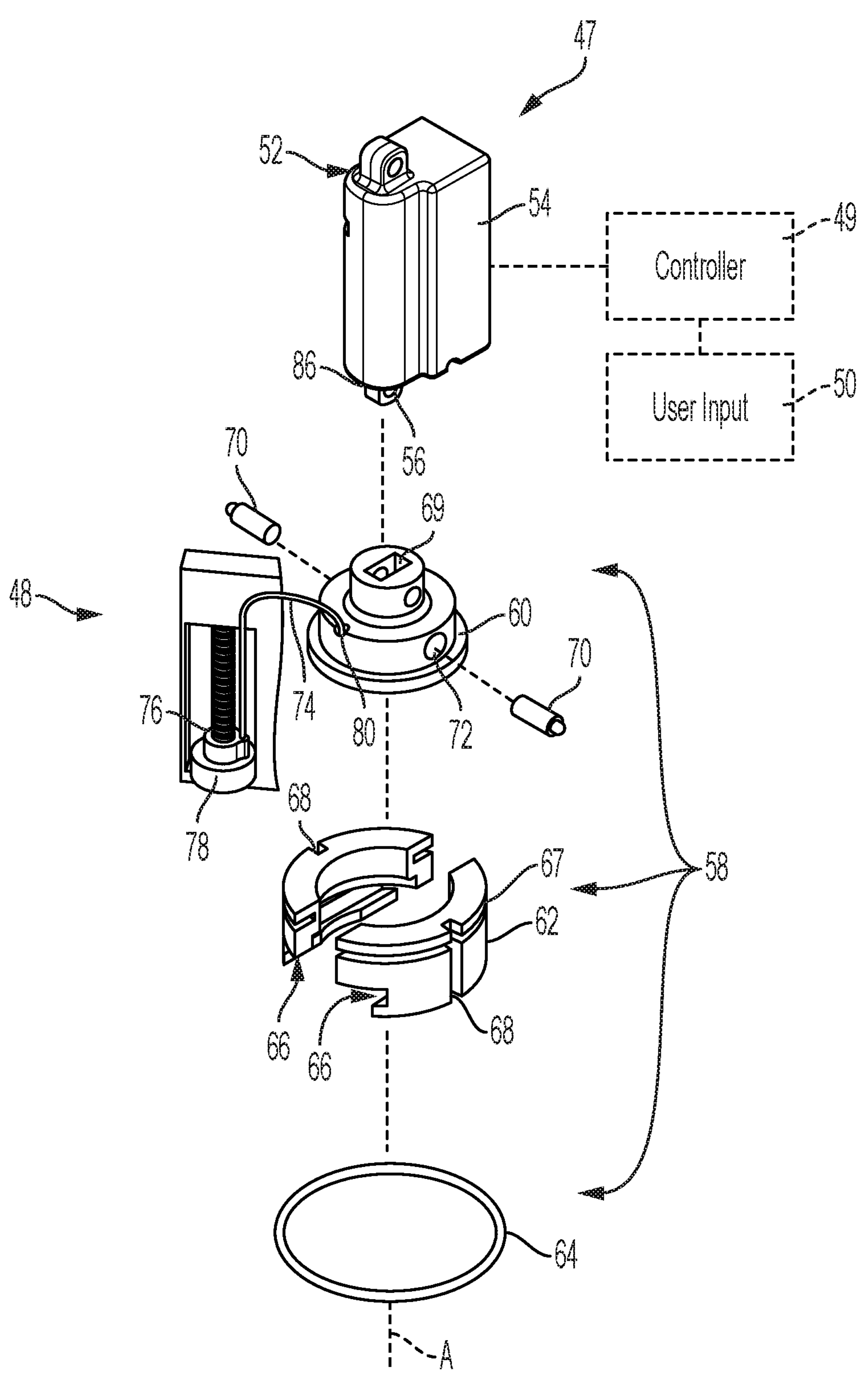
FIG. 2 is exploded perspective view of the drive components of the medication delivery device of FIG. 1.

FIGS. 1 and 2 illustrate an exemplary electronic embodiment of a medication delivery device 10. Illustratively, the medication delivery device 10 has an injector pen-like shape, although other shapes may alternatively be used. The medication delivery device 10 generally includes a reusable portion 12 and a disposable portion 14, which may also be referred to as a drug carrying portion. The reusable portion 12 facilitates delivery of a medication (shown elsewhere) from the disposable portion 14. In addition, the reusable portion 12 detachably couples to the disposable portion 14 such that after the medication has been delivered from the disposable portion 14, the disposable portion 14 may be detached from the reusable portion 12 and discarded. Another disposable portion (not shown—for example, having the same or different features than the disposable portion 14) may then be attached to the reusable portion 12, and the medication delivery device 10 is thereby ready for subsequent use. Although the device described herein may reference the use of a disposable portion and a reusable portion, it is understood that the disclosure herein is not limited to a reusable device, and the subsystems of the device may be incorporated into a completely disposable device (that is, the disposable and reusable portions are permanently coupled to one another and configured for single exhaustion of the medication from the syringe in either a single use or additional uses.

The medication delivery device 10 also includes a proximal end 16 and an opposite distal end 18. During use of the medication delivery device 10, the proximal end 16 would be farther from the patient and configured to be actuated by the user, and the distal end 18 would be closer to the patient and configured to deliver the medication (shown elsewhere) to the patient. The medication delivery device 10 also includes a longitudinal axis A extending between the proximal end 16 and the distal end 18.

Disposable portion 14 may be a single or multi-use disposable therapeutic delivery apparatus that includes syringe 35. Syringe 35 can be one of a variety of types and/or sizes of syringes including NeoPak™ syringe in various sizes, such as for example, 0.5 mL, 1 mL, 1.5 mL, 2 mL or other sizes. In some cases, syringe 35 is a single use syringe where all of the medication is delivered to the patient in one dose, while in other cases, syringe 35 is a multi-use syringe where multiple doses of the medication are delivered to the patient from the same syringe 35.

The illustrated syringe 35 includes barrel 36, piston 38, and needle 40. Barrel 36 is a cylindrical container that is configured to contain the medication 37. Piston 38 is positioned within barrel 36, and when force is applied to the top surface (e.g., the proximal end) of piston 38, the piston 38 moves in a longitudinal direction along the longitudinal axis A towards the distal end 18 of medication delivery device 10. In this case, the medication 37 can be forced (e.g., expelled) through an opening in needle 40 and delivered into the patient's skin. In some cases, syringe 35 is supplied with a removable needle shield (RNS) 42 coupled to needle 40. RNS 42 may protect the user from inadvertent injury by covering the sharp end of needle 40 until it is time to administer a dose of medication 37.

Device 10 described herein, such as, for example, an autoinjector, may be other kinds of injector devices that may incorporate the elements of this disclosure, may further comprise medication, such as for example, within a reservoir defined by the barrel 36 provided by the syringe 35. In another embodiment, a system may comprise one or more devices including device and a medication. The term "medication" refers to one or more medications including but not limited to insulins, insulin analogs such as insulin lispro or insulin glargine, insulin derivatives, GLP-1 receptor agonists such as dulaglutide or liraglutide, glucagon, glucagon analogs, glucagon derivatives, gastric inhibitory polypeptide (GIP), GIP analogs, GIP derivatives, oxyntomodulin analogs, oxyntomodulin derivatives, therapeutic antibodies and any medication that is capable of delivery by the above device. The medication as used in the device may be formulated with one or more excipients. The device 10 is operated in a manner generally as described above by a patient, caregiver or healthcare professional to deliver medication to a person.

Disposable portion 14 may also include a carrier 44 coupled to a proximal end 16 of barrel 36. Carrier 44 can be used to couple the disposable portion 14 with the reusable portion 12. For example, carrier 44 includes a pair of protrusions 46 (e.g., arms, wings, etc.), which protrude radially from carrier 44. Protrusions 46 can slide radially into a component of the reusable portion 12 in a radial direction R (e.g., a guide 62 of a shuttle 58, as discussed in further detail below).

The reusable portion 12 includes a housing 20. Housing 20 can be a generally cylindrical structure (or other geometry) that both contains and protects the various components of medication delivery device 10. Housing 20 can be formed from a variety of materials including plastic, metal, ceramic, or other suitable materials to provide rigidity to the exterior of medication delivery device 10.

Housing 20 may house the drive components of medication delivery device 10. The drive components of medication delivery device 10 can include an electromechanical actuator assembly 47 and shuttle 58. Actuator assembly 47 may drive the longitudinal extension and retraction of disposable portion 14 through housing 20. As best illustrated in FIG. 2, actuator assembly 47 can include an actuator motor 54 coupled to an electromechanical linear actuator 52 (also referred to herein as a linear drive component). Actuator 52 includes a longitudinal member 86 that extends longitudinally from the bottom portion of actuator 52. Actuator motor 54 may attach to actuator 52 and drive the longitudinal extension and retraction of longitudinal member 86 about longitudinal axis A. The extension and retraction of longitudinal member 86 by actuator 52 may be activated by a user input 50, which may be in electronic communication with motor via an electronic controller 49 as shown in FIG. 2 or physical communication with actuator motor 54.

Actuator 52 may include a foot 56 coupled to a shuttle 58. Shuttle 58 is a component that both couples with the disposable portion 14 and guides the movement of disposable portion 14 longitudinally through housing 20. Shuttle 58 includes a drive adaptor 60, a guide 62, and an O-ring 64. Drive adaptor 60 includes a recess 69 that accepts foot 56 of actuator 52 and couples actuator assembly 47 with shuttle 58. Guide 62 may be a two-part structure that circumferentially surrounds drive adaptor 60. The two parts of guide 62 may be secured around the circumference of drive adaptor 60 by O-ring 64. O-ring 64 is formed from an elastic material and is housed in a circumferential recess 67 of guide 62. In this case, the elasticity of O-ring 64 holds the two halves of guide 62 together to retain drive adaptor 60 within guide 62, effectively coupling the three structures to form shuttle 58. As such, shuttle 58 moves in concert with actuator assembly 47 by the coupling of actuator assembly 47 to drive adaptor 60.

Guide 62 includes radial recesses 66 which accept carrier 44 of disposable portion 14. As described above, disposable portion 14 includes carrier 44, which includes protrusions 46. Radial recesses 66 in guide 62 can accept protrusions 46 when carrier 44 is inserted into guide 62 in the radial direction R (e.g., when carrier 44 is slid into guide 62 in a horizontal direction). In this case, the compressive forces supplied by the elastic material of O-ring 64 holds carrier 44 within guide 62. These forces couple's guide 62 with carrier 44 which effectively couples disposable portion 14 with reusable portion 12. As such, actuator assembly 47 can move disposable portion 14 longitudinally through housing 20 by the coupling of shuttle 58 to both actuator assembly 47 and disposable portion 14 (e.g., by the coupling of carrier 44 with guide 62).

Returning to FIG. 1, housing 20 includes a passageway 28 extending along longitudinal axis A between a portion of the proximal end 16 and the distal end 18 of housing 20. Passageway 28 can be a generally hollow and cylindrical passageway defined by an interior surface 30 of housing 20. Interior surface 30 can be a cylindrical surface including one or more rails 32. Rails 32 may project inwardly and extend longitudinally with passageway 28 and may be used to guide movement of internal components of medication delivery device 10 when injecting a patient. For example, as shown in FIG. 2, guide 62 can include one or more lateral recesses 68. Lateral recesses 68 may accept rails 32 and fix the angular position of shuttle 58 within passageway 28. In this case, rails 32 guide the movement of shuttle 58 along longitudinal axis A within passageway 28 when actuator 52 extends and retracts longitudinal member 86.

The illustrated housing 20 also includes opening 34 in the side of housing 20 that is configured to receive disposable portion 14. For example, disposable portion 14 can be inserted by the user into opening 34 in a radial direction R (e.g., perpendicular or substantially perpendicular (+/−5 degrees) to longitudinal axis A). In this case, opening 34 is sized to receive the entire length and the entire width of disposable portion 14 so that the patient can insert disposable portion 14 with a simple sliding movement and without any rotation of disposable portion 14 about longitudinal axis A. This opening 34 allows for the radial recesses 66 in guide 62 to accept the protrusions 46 of carrier 44. Opening 34 can accommodate a variety of sizes of disposable portions 14. As discussed above, disposable portion 14 can include 1 mL and 2 mL variants of syringes 35, and as such, opening 34 can be sized to accommodate both types of disposable portions 14. In other cases, disposable portions 14 could also be larger or smaller than 1 mL and/or 2 mL, and have different dimensions (e.g., length and width) than these embodiments. In these cases, opening 34 may be sized to accommodate these dimensional variations in disposable portion 14.

In some cases, opening 34 may be enclosed by a door (not shown) coupled to housing 20, however, in the illustrated embodiment, opening 34 does not contain a door and is an uncovered opening as shown in FIG. 1. In embodiments in which the opening 34 is uncovered, the entire length and width of the syringe 35 may be visible inside housing 20 through the opening 34 once loaded. In other words, the housing 20 may lack any structures that obstruct the view of syringe 35.

Housing 20 can also include a base 22. Base 22 can be a generally triangular structure with a flat bottom surface 24 that extends perpendicularly to longitudinal axis A. Bottom surface 24 of base 22 allows for base 22 to contact the surface of a patient's skin in a substantially perpendicular orientation when delivering the medication 37. Bottom surface 24 also allows for medication delivery device 10 to stand on a flat surface (e.g., a table). Base 22 can also be used to attach to a basecap (shown elsewhere), which can wirelessly charge medication delivery device 10.

Bottom surface 24 includes opening 26 which allows for a portion of disposable portion 14 to protrude from housing 20 when injecting a patient. For example, when actuator 52 extends disposable portion 14 towards the distal end 18 of medication delivery device 10, a portion of needle 40 extends from opening 26 below the bottom surface 24 of base 22 and into the patient's skin when delivering the medication 37. Once the medication 37 within disposable portion 14 has been delivered, disposable portion 14 can be ejected from reusable portion 12 through opening 26.

Returning to FIG. 2, shuttle 58 can include one or more plungers 70 (illustratively, a pair of plungers 70) that aid in the ejection of disposable portion 14 from reusable portion 12. As discussed previously, shuttle 58 includes drive adaptor 60 where O-ring 64 holds the two halves of guide 62 together to contain drive adaptor 60. Plungers 70 are recessed into channels 72 within drive adaptor 60. Plungers 70 may include springs (not shown) that provide tension against the two halves of guide 62 in a radially outward direction that can separate the two halves of guide 62.

Medication delivery device 10 also includes liquid expulsion assembly 48. Liquid expulsion assembly 48 can be used to expel the medication 37 from the disposable portion 14 and into the patient. Liquid expulsion assembly 48 includes a flexible member 74 as a plunger, lead screw 76 and motor 78 as a plunger drive. Flexible member may comprise a metal wire, polymer or rubber ribbon, a polymer or metal coil. In one embodiment, the flexible member 74 may comprise of a wire may be fed from liquid expulsion assembly 48 and through a hole 80 in drive adaptor 60 of shuttle 58. As described previously, guide 62 receives carrier 44 and couples disposable portion 14 with shuttle 58. The hole 80 in shuttle 58 receives flexible member 74 fed from liquid expulsion assembly 48 and allows for flexible member 74 to extend into barrel 36 of syringe 35 (FIG. 1). As described previously, syringe 35 includes piston 38 positioned within barrel 36. In this case, flexible member 74 is fed from liquid expulsion assembly 48 and supplies a longitudinally downward force on piston 38 as the motor 78 moves the lead screw 76 upward. This downward force causes piston 38 to travel longitudinally downward within barrel 36 and force liquid (e.g., the medication 37) out of needle 40 and into the patient. Flexible member 74 can then be retracted in a longitudinally upward direction by liquid expulsion assembly 48 and removed from barrel 36 as the motor 78 moves the lead screw 76 downward. In this case, disposable portion 14 can be effectively removed from reusable portion 12 since flexible member 74 is no longer in disposable portion 14. Alternative mechanisms of extending and retracting flexible member 74 may be incorporated into liquid expulsion assembly 48. Flexible member 74 is a flexible member that can be made of a variety of materials, such as Nitinol. The flexibility of flexible member 74 enables the flexible member 74 to move laterally upwards and out of liquid expulsion assembly 48, horizontally through housing 20 and into drive adaptor 60 and longitudinally downwards into barrel 36 by a supplied force to one end of flexible member 74 (e.g. by lead screw 76). Although illustrated as such, in some cases medication delivery device 10 may not use a liquid expulsion assembly 48, and rather a portion of longitudinal member 86 can supply the downward force on piston 38 and causes piston 38 to travel longitudinally downward within barrel 36 and force liquid (e.g., the medication 37) out of needle 40 and into the patient. Although one embodiment of the liquid expulsion assembly 48 is described, other examples of liquid expulsion assemblies that include flexible plunger members can be found in the following U.S. Pat. Nos. 9,289,556, 7,220,248, 8,376,993, 6,302,869, and 10,173,012.

In operation, controller 49 (FIG. 2) of medication delivery device 10 can include components and features that allows for wireless communication with a remote system (such as an application on a smart device, a server, or other cloud-based systems). These systems can be used to control the operation of medication delivery device 10, automating some of the steps of delivering a medication 37 to a patient. For example, controller 49 of medication delivery device 10 may receive a command to activate (e.g., wake up) from an in-active state (e.g., sleep) from a remote system. This command may trigger the medication delivery device 10 to turn on and begin preparation to deliver a medication 37 to a patient. At this point, medication delivery device 10 can be removed from a basecap or other charging mechanism (not shown) by the user.

The user, either prior to removal or after removal from the basecap, can radially insert the disposable portion 14 into the reusable portion 12 through opening 34 by radially sliding the carrier 44 into the guide 62 to couple the disposable portion 14 with shuttle 58, as described above. The radial insertion of the disposable portion 14 into the reusable portion 12 through the opening 34 carries certain benefits. First, the structure is simple, since the opening 34 directly accesses the shuttle 58 (e.g., additional structures are not required to orient disposable portion 14). Furthermore, due to the size of opening 34, the insertion process is also simple (e.g., radial insertion of the disposable portion 14 is possible, rather than angled insertion of the disposable portion 14). Also, additional structures such as doors or other enclosing structures can be avoided, if desired. As such, the disposable portion 14 may remain visible throughout the entire insertion process.

FIGS. 3-7 illustrate the steps of delivering a medication 37 from the medication delivery device 10.

Figure 3:
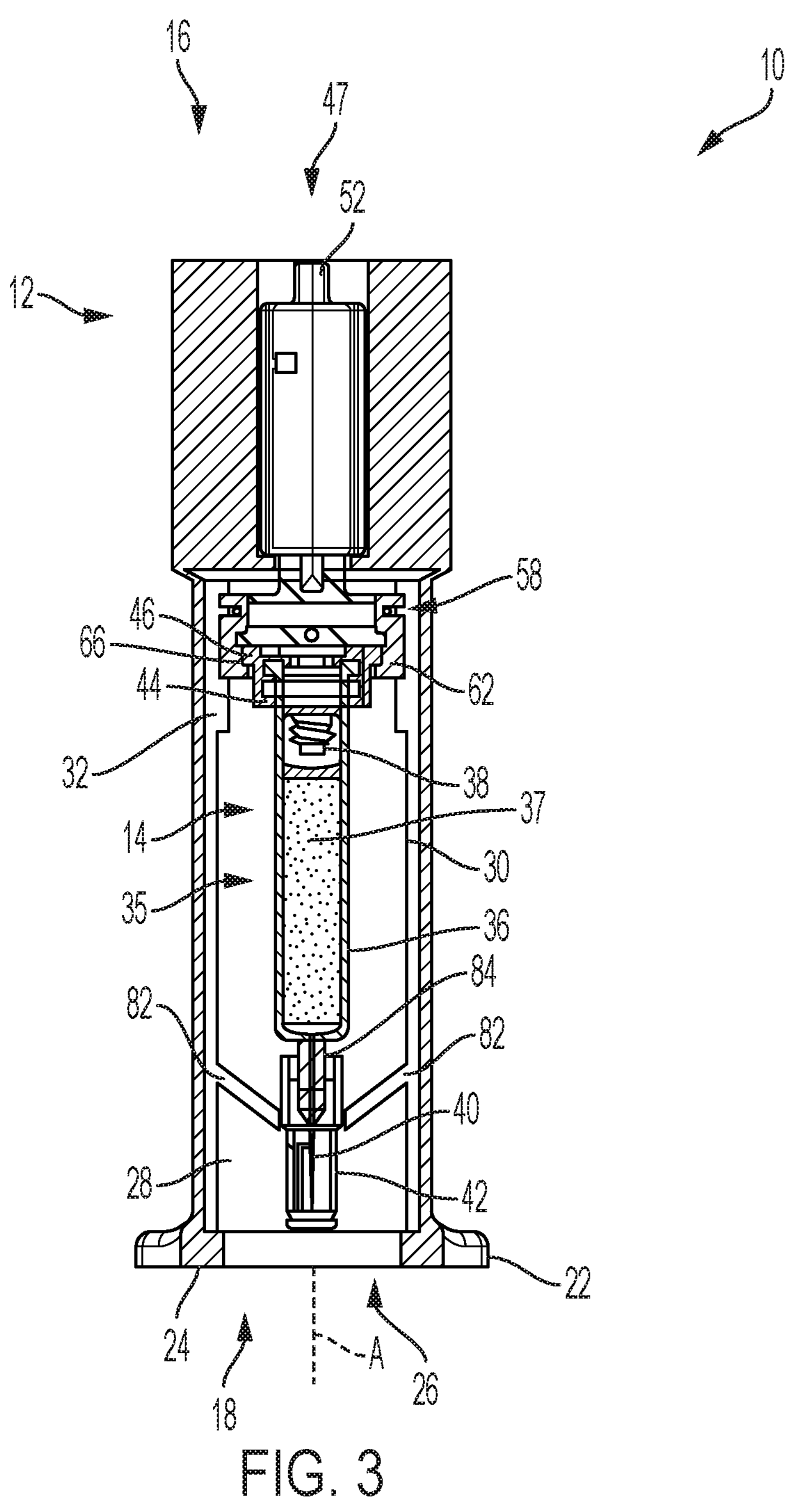
FIG. 3 is a side view of the medication delivery device of FIG. 1 in a first state.

FIG. 3 shows the medication delivery device 10 in a stowed state with the disposable portion 14 loaded into the reusable portion 12. The protrusions 46 of the carrier 44 are captured within the recesses 66 of the guide 62. In this stowed state, the needle 40 is raised above the bottom surface 24 of the housing 20 and covered by the RNS 42. The patient can view the correct insertion of the carrier 44 into the guide 62 through opening 34 (FIG. 1). In some cases, the disposable portion 14 may have been pre-inserted into reusable portion 12 before the activation command. Sensors associated with controller 49 (FIG. 2) of medication delivery device 10 (such as proximity sensors, light sensors, weight sensor, etc.), may sense the coupling of disposable portion 14 with shuttle 58 and determine that medication delivery device 10 is in the stowed state, ready for future injection of the medication 37 into the patient.

Figure 4:
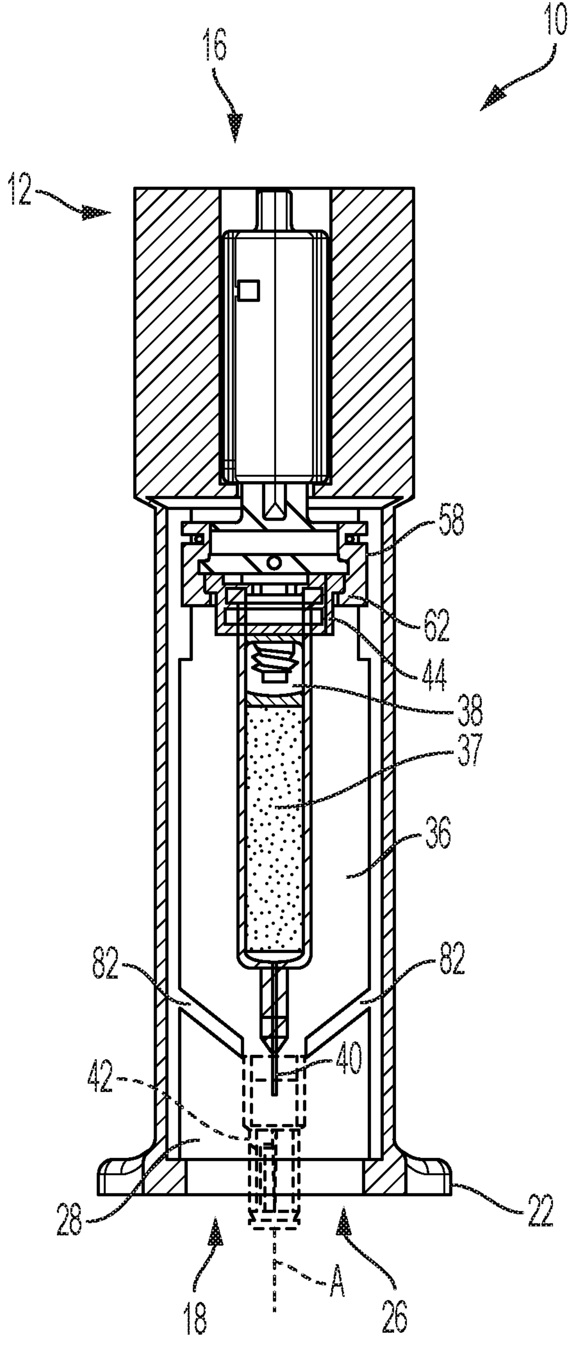
FIG. 4 is a side view of the medication delivery device of FIG. 1 in a second state.

FIG. 4 shows the medication delivery device 10 in a pre-armed state (in broken lines) and an armed state (in solid lines). Interior surface 30 of housing 20 may include one or more fingers 82 (in this case, illustrated as a pair of fingers 82). Fingers 82 may be flexible components positioned towards the distal end 18 of passageway 28.

In the pre-armed state of FIG. 4, actuator assembly 47 may be activated by controller 49 (FIG. 2) (via user input 50, a remote system, or by the internal software/firmware of medication delivery device 10) to remove RNS 42 from needle 40. In this case, actuator assembly 47 is activated to extend actuator 52 in a longitudinally downward direction toward the distal end 18 of passageway 28 where RNS 42 contacts fingers 82. RNS 42 may pass over fingers 82 until fingers 82 contact the upper surface 84 of RNS 42 (e.g., the joint of the top of RNS 42 and the base of barrel 36).

In the armed state of FIG. 4, actuator 52 may retract longitudinally upwards and the force provided by fingers 82 against RNS 42 may decouple RNS 42 from needle 40. RNS 42 may fall away from needle 40 and into a container (e.g., a sharps container), or may be removed by the user. The process of removing RNS 42 from needle 40 may be triggered by proximity of medication delivery device 10 to a designated sharps container, to the patient, or by other means. Once RNS 42 has been removed from needle 40, medication delivery device 10 may be considered in the armed state (in comparison to the stowed state of FIG. 3 with RNS 42 still attached to needle 40) where medication delivery device 10 can receive a command to inject the patient. For example, once medication delivery device 10 is in the armed state (e.g., as confirmed by sensors within medication delivery device 10), injection of the medication 37 can be triggered by controller 49 (FIG. 2) (via user input 50, the remote system, or the software/firmware of the medication delivery device 10). User input 50 can be a variety of trigger mechanisms such as a button. When the patient depresses user input 50, a system check may be performed by controller 49 of medication delivery device 10 to ensure that the medication delivery device 10 is armed and ready to deploy the medication 37. At this point, medication delivery device 10 may receive approval and a corresponding injection command to initiate injection of the medication 37 (e.g., either from the remote system, or via the internal software or firmware of medication delivery device 10) and progresses from the armed state to a deployed state, which is described further below.

Figure 5:
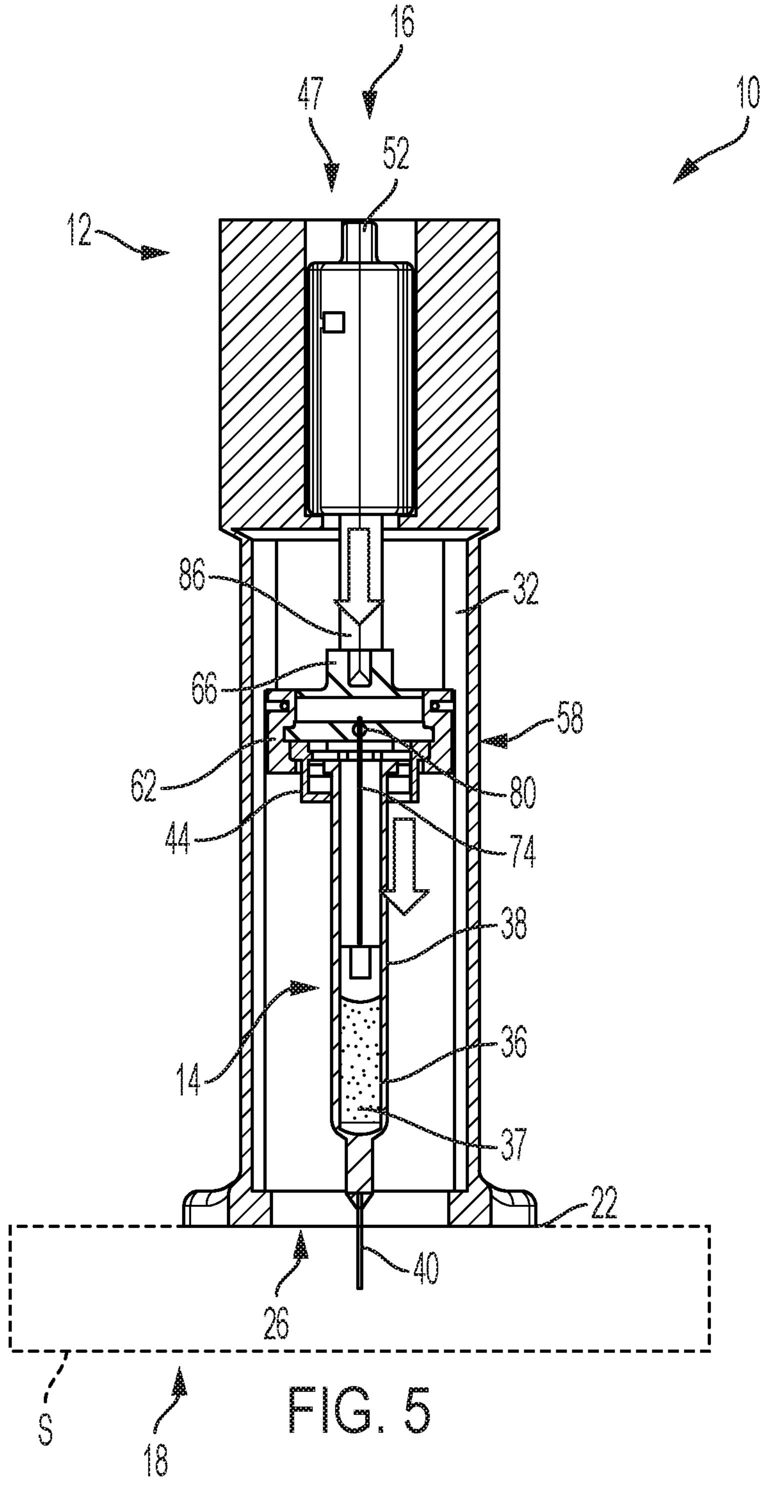
FIG. 5 is a side view of the medication delivery device of FIG. 1 in a third state.

FIG. 5 illustrates such an injection of the medication 37 into the patient in a deployed state. Once the injection command is received, actuator assembly 47 extends longitudinal member 86 of actuator 52 towards the distal end of 18 of passageway 28. In this case, the shuttle 58 (as coupled with the foot 56 of actuator 52) extends longitudinally downward along rails 32 of housing 20, partially (or fully) extending needle 40 from opening 26 in base 22 of housing 20 and into the patient's skin S. Medication delivery device 10 may sense the penetration of the patients skin by needle 40 (e.g., by force sensors associated with actuator 52, proximity sensors associated with shuttle 58, and/or light sensors associated with the position of syringe 35) and initiate injection of the medication 37 into the patient. In this case, actuator assembly 47 may communicate with liquid expulsion assembly 48 (FIG. 2) and liquid expulsion assembly 48 may feed flexible member 74 into barrel 36 and force piston 38 towards the distal end 18 of barrel 36 thus expelling the medication 37 from needle 40 and into the patient's skin S. Flexible member 74 may be fed into barrel 36 until piston 38 has reached the bottom of barrel 36 indicating that all of the medication 37 has been delivered. The position of piston 38 can be determined by a force sensor or stops on motor 78 of liquid expulsion assembly 48 or via a proximity (e.g., light) sensor on the interior surface 30 of housing 20, for example. The carrier 44 and the upper end of the syringe 35 may remain visible through the opening 34 of the housing 20 (FIG. 1) in this deployed state.

Figure 6:
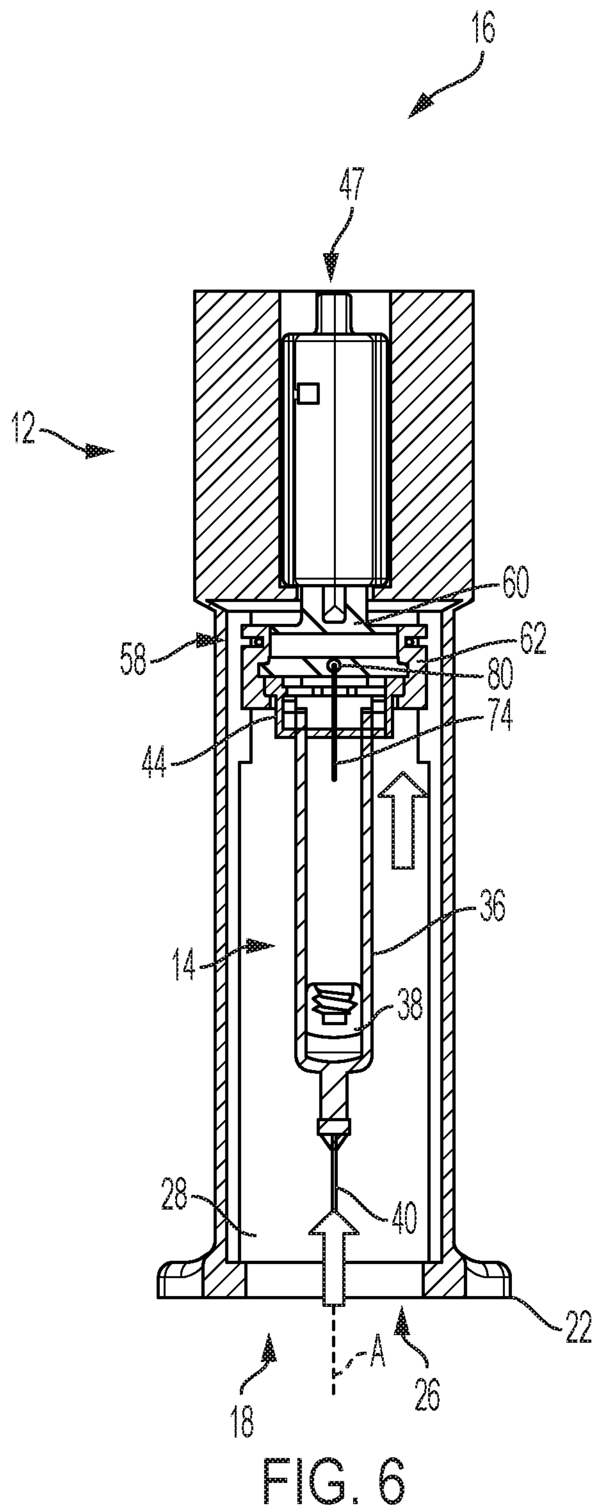
FIG. 6 is a side view of the medication delivery device of FIG. 1 in a fourth state.

As illustrated in FIG. 6, once the medication 37 has been delivered to the patient, needle 40 may be retracted back into opening 26 in base 22 of housing 20. In this case, a longitudinal member 86 of actuator 52 may be retracted, and shuttle 58 may travel longitudinally upwards towards the proximal end 16 of medication delivery device 10. Flexible member 74 may also be retracted back towards liquid expulsion assembly 48 (FIG. 2) (e.g., flexible member 74 may be retracted towards the hole 80 in drive adaptor 60). In this case, medication delivery device 10 is now in a retracted state.

Once in the retracted state of FIG. 6, controller 49 (FIG. 2) of medication delivery device 10 may receive an ejection command to eject the spent disposable portion 14 from reusable portion 12. This ejection command can occur based on the proximity of medication delivery device 10 to a container (such as a sharps container), or may be based upon other factors (e.g., an input on an application associated with medication delivery device 10, time, a patient's manual removal indication, etc.).

Figure 7:
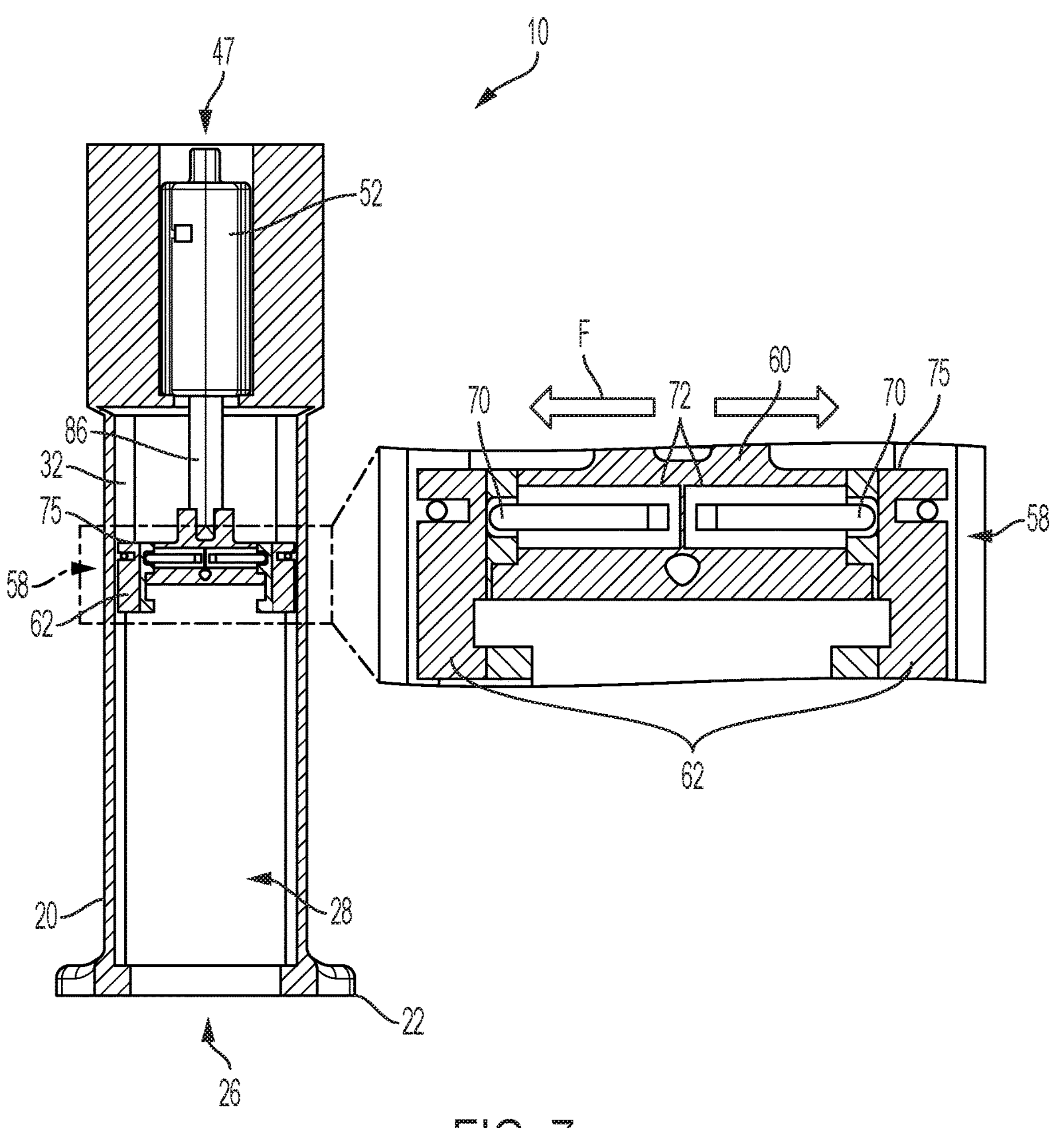
FIG. 7 is a perspective view of drive components of the medication delivery device of FIG. 1 in a fourth state

FIG. 7 shows the medication delivery device 10 in an ejected state. As discussed previously, drive adaptor 60 includes plungers 70 that extend radially outwards from drive adaptor 60 to force the two halves of guide 62 apart. Once the ejection command is received by medication delivery device 10, actuator assembly 47 may be activated to fully extend longitudinal member 86 of actuator 52 towards the distal end 18 of passageway 28. The shuttle 58 may travel longitudinally downward along rails 32 of housing 20 as in the deployed state (FIG. 5). However, in the released state, the shuttle 58 may continue further downward along rails 32 past the deployed state until a transition point 75 is reached by shuttle 58. At this transition point 75, rails 32 decrease in radial thickness, which causes the two halves of guide 62 to separate under the radially outward force F of the plungers 70. The two halves of guide 62 may separate to a slightly larger extent than the length of protrusions 46 of disposable portion 14 (FIG. 3), thereby freeing protrusions 46 from guide 62 of shuttle 58. Disposable portion 14 then decouples from shuttle 58 and drops out of opening 26 in base 22 of housing 20 under the force of gravity. The spent disposable portion 14 may drop into a sharps container to dispose of the spent disposable portion 14.

Once the medication delivery device 10 is in the ejected state, the medication delivery device 10 may enter a sleep and/or standby mode (e.g., a low power mode). Medication delivery device 10 can be replaced onto the charging basecap, or another wireless charging structure, to charge medication delivery device 10 and prepare for another injection of a medication 37. Controller 49 (FIG. 2) of medication delivery device 10 can also send a command and/or report to the remote system indicating that the medication 37 has been delivered, including a timestamp for the delivery. The medication delivery device 10 can then be awoken for a second time and the patient can insert another disposable portion 14 through opening 34 in housing 20 for subsequent injection. The medication 37 may be the same medication 37, or may be different medication, and as discussed previously, the reusable portion 12 can accommodate different sizes of disposable portions 14.

FIGS. 8-13 illustrate an exemplary mechanical embodiment of medication delivery device 11. The above-described electronic embodiment of medication delivery device 10 and the mechanical embodiment of medication delivery device 11 are substantially similar in features and operation, with like reference numerals designating the similar structures between the two devices. As such, the prior discussion of medication delivery device 10 is incorporated herein. Medication delivery device 11 differs from medication delivery device 10 in some aspects/features, as follows.

Figure 8:
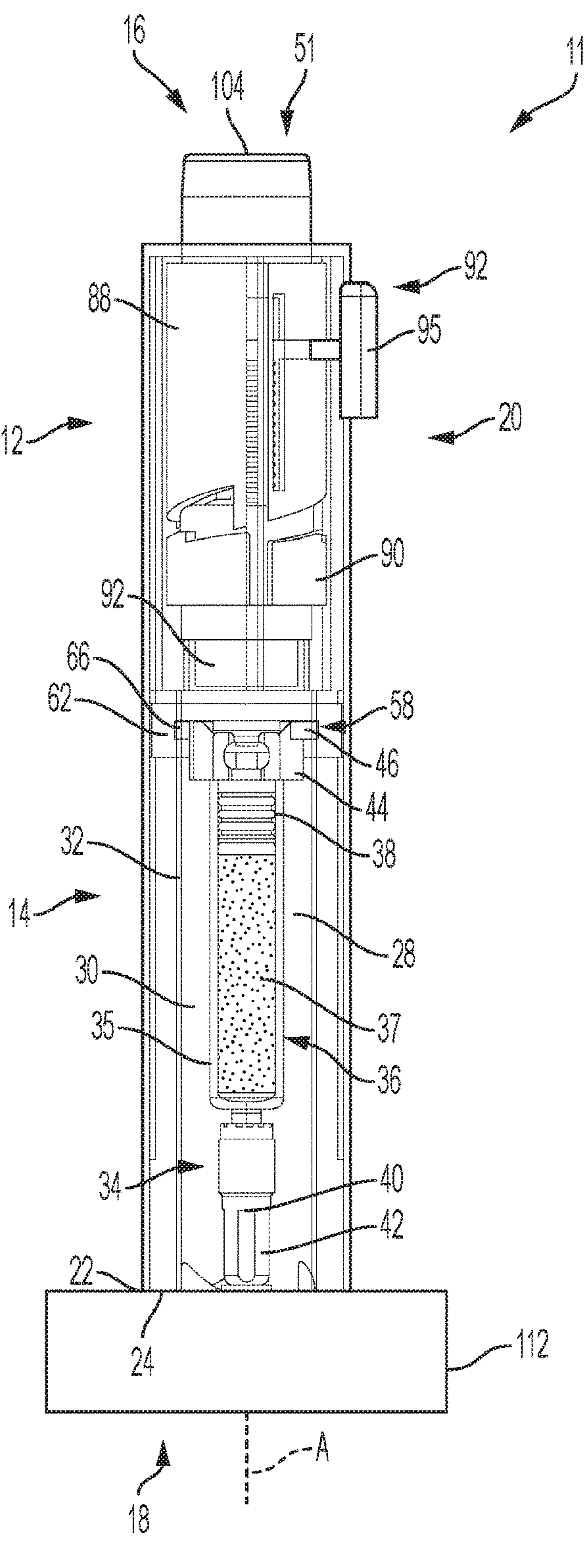
FIG. 8 is a side view of a medication delivery device in a first state according to embodiments of the present disclosure.
Figure 13:
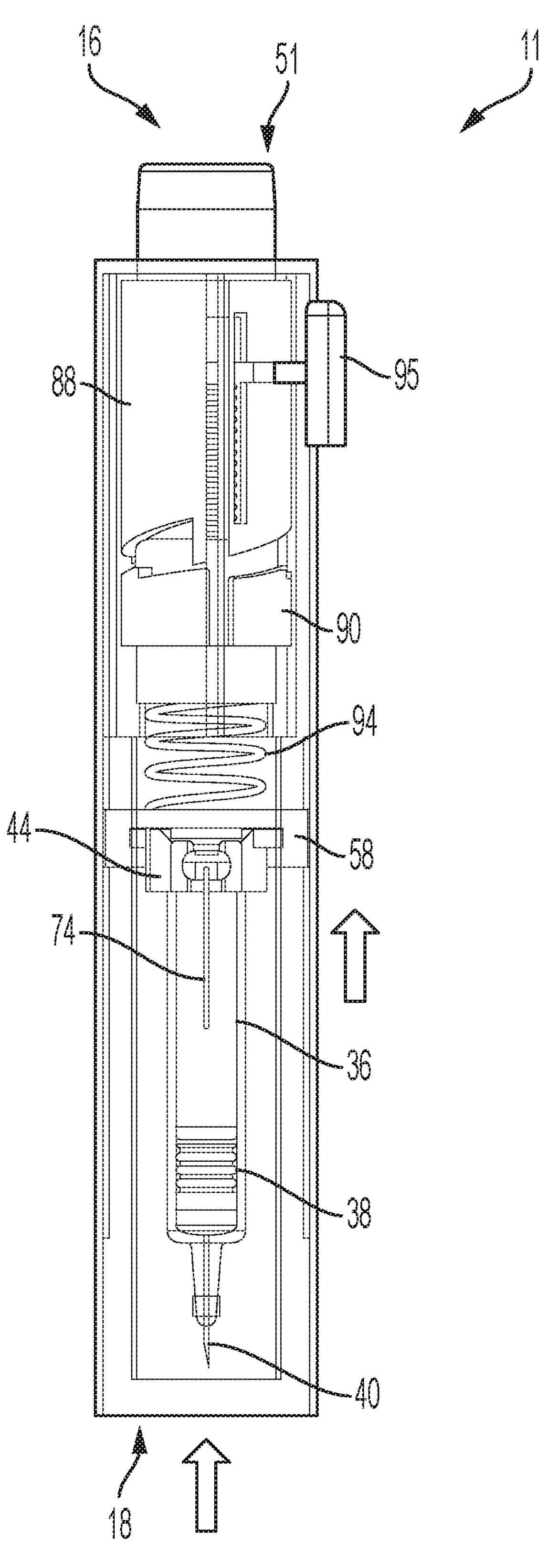
FIG. 13 is a side view of the medication delivery device of FIG. 8 in a fifth state.

As illustrated in FIG. 8, medication delivery device 11 includes a mechanical actuator assembly 51 rather than the electromechanical actuator assembly 47 of medication delivery device 10. The mechanical actuator assembly 51 of medication delivery device 11 includes a user input in the form of a thruster button 88, a cam 90, a lock assembly 92, and a spring 94 (FIG. 13). As with medication delivery device 10, medication delivery device 11 is operable to move shuttle 58 longitudinally across rails 32 on the interior surface 30 of housing 20. However, medication delivery device 11 moves shuttle 58 longitudinally along passageway 28 by operating the mechanical actuator assembly 51 to move cam 90 and/or lock assembly 92.

Referring still to FIG. 8, medication delivery device 11 may also include a basecap 112. Similar to medication delivery device 10, the basecap 112 may provide charging capabilities for the electrical components associated with medication delivery device 11. Additionally, basecap 112 may be used to remove RNS 42 from needle 40, as described further below.

As with medication delivery device 10, medication delivery device 11 can include components and features that allows for wireless communication with a remote system (such as an application on a smart device, a server, or other cloud-based systems). These systems can be used to control the operation of medication delivery device 11 and may automate some of the steps of delivering a medication 37 to a patient. For example, and as illustrated in FIG. 8, as with medication delivery device 10, medication delivery device 11 may receive a command to activate (e.g., wake up) from an in-active state (e.g., sleep) from a remote system. This activation command may trigger the medication delivery device 10 to turn on, and begin preparation to deliver a medication 37 to a patient. At this point, the patient can radially insert the disposable portion 14 through opening 34 of reusable portion 12 in the same manner described above with respect to medication delivery device 10.

FIG. 8 shows the medication delivery device 11 in a stowed state with the disposable portion 14 loaded into the reusable portion 12. The protrusions 46 of the carrier 44 are captured within the recesses 66 of the guide 62. In this stowed state, the needle 40 is raised above the base 22 of the housing 20 and covered by the RNS 42. The basecap 112 is also coupled to the base 22 of the housing 20.

Figure 9:
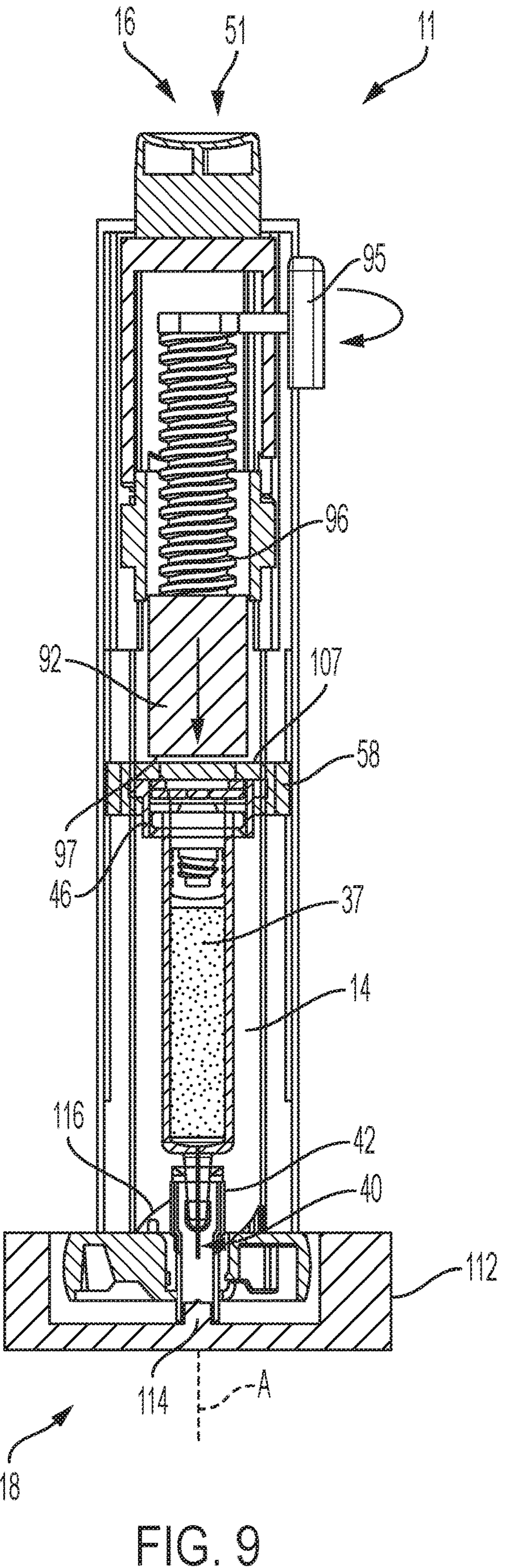
FIG. 9 is a side view of the medication delivery device of FIG. 8 in a second state.

FIG. 9 shows the medication delivery device 11 in a pre-armed state with the RNS 42 being removed from the needle 40. This pre-armed state may be achieved by operating the lock assembly 92. For example, as illustrated in FIG. 9, grip 95 of lock assembly 92 may receive a tangential force in relation to longitudinal axis A (e.g., in a counterclockwise direction) which may cause the lock assembly 92 to rotate and move longitudinally downwards about threads 96 associated with lock assembly 92. This movement may cause the bottom surface 97 of lock assembly 92 to contact the top surface 107 of the shuttle 58. In this case, the longitudinal movement of lock assembly 92 causes shuttle 58 to move longitudinally downwards towards the distal end 18 of the housing 20.

Basecap 112 of FIG. 9 includes a recess 114 that accepts RNS 42 when disposable portion 14 moves longitudinally downwards and one or more arms 116 that contact a portion of RNS 42 when RNS 42 is inserted into basecap 112. In this case, arms 116 may fix RNS 42 within recess 114. When grip 95 is rotated by the patient, shuttle 58 moves longitudinally downwards, forcing RNS 42 into recess 114. Arms 116 contacts RNS 42 and hold RNS 42 in recess 114. At this point, basecap 112 may communicate with the remote system and/or medication delivery device 11, indicating that RNS 42 can be safely decoupled from needle 40 to arm medication delivery device 11.

Figure 10:
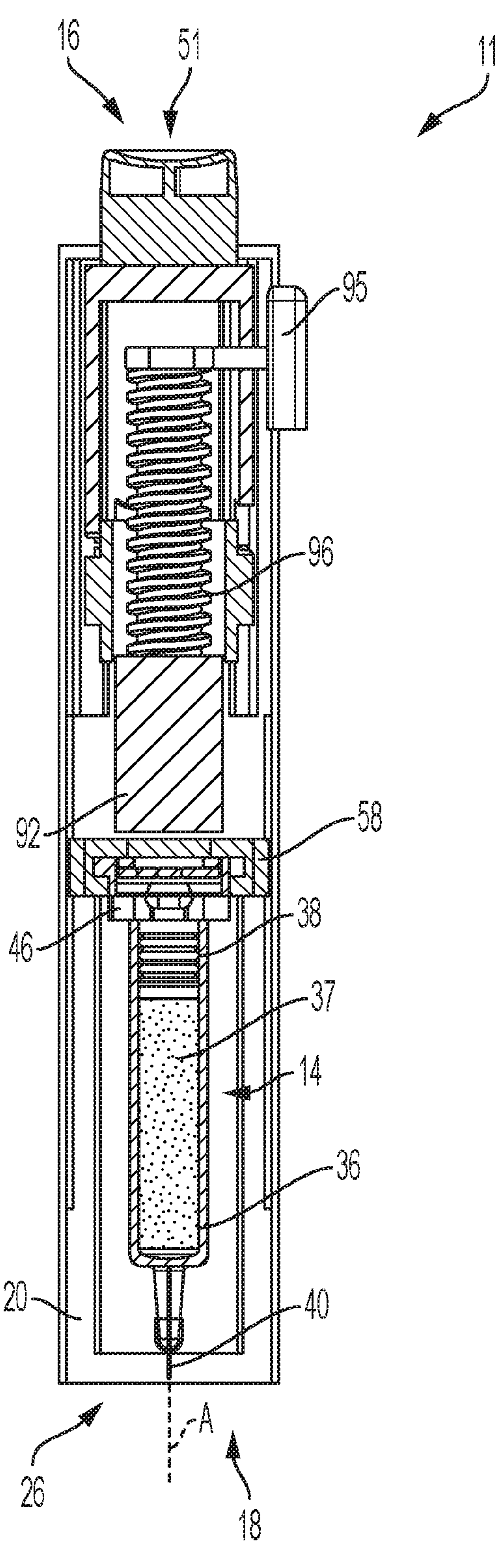
FIG. 10 is a side view of the medication delivery device of FIG. 8 in a third state.

FIG. 10 shows the medication delivery device 11 in an armed state with the RNS 42 removed from the needle 40. The user has pulled longitudinally upwards on the housing 20 of medication delivery device 11 to detach the base 22 of medication delivery device 11 from basecap 112 (FIG. 9) and effectively detached RNS 42 from needle 40. Basecap 112 may retain RNS 42 for later recoupling of RNS 42 with needle 40 after delivery of the medication 37.

Figure 11:
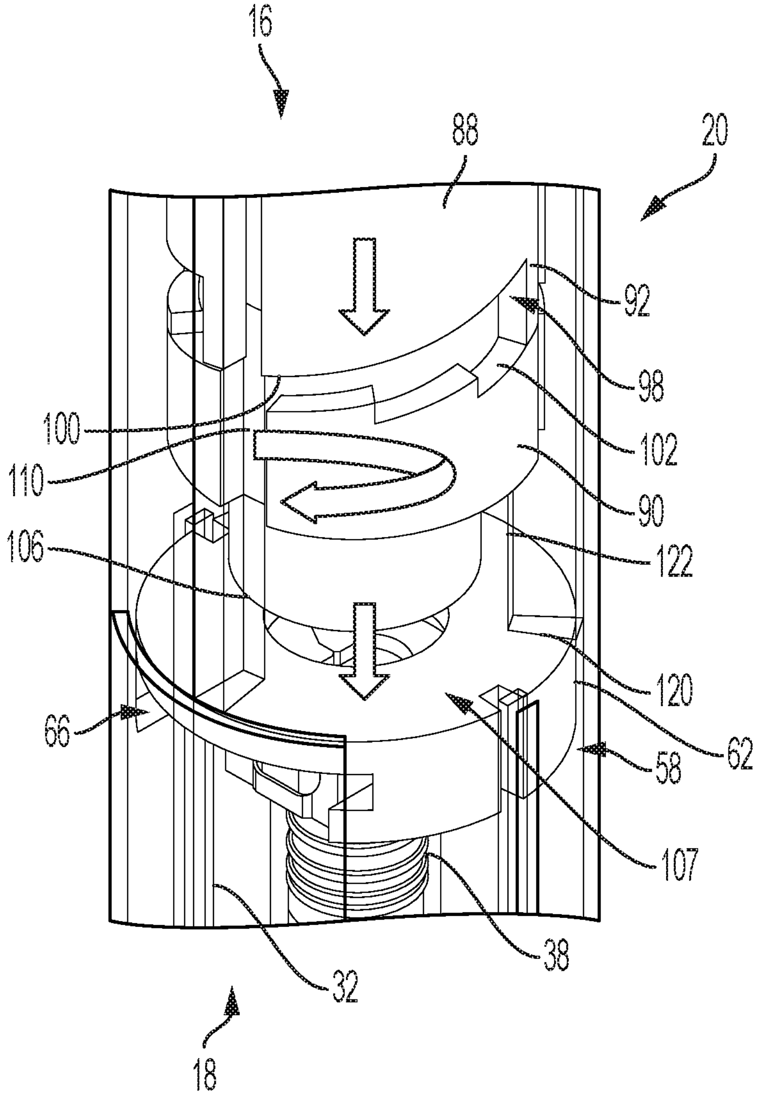
FIG. 11 is a perspective view of drive components of the medication delivery device of FIG. 8.
Figure 12:
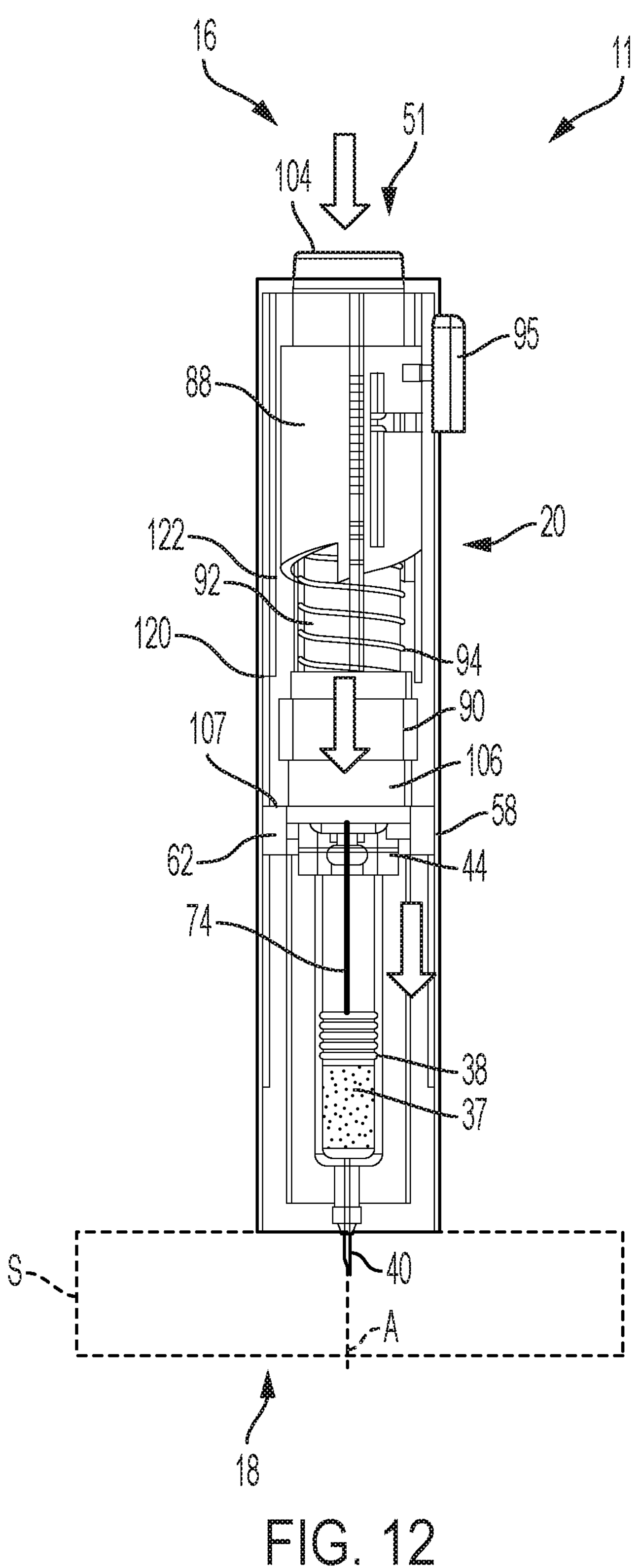
FIG. 12 is a side view of the medication delivery device of FIG. 8 in a fourth state.

FIGS. 11 and 12 show the medication delivery device 11 in a deployed state. As noted above, actuator assembly 51 of medication delivery device 11 may include the thruster button 88 and the cam 90, wherein the thruster button 88 includes a plurality of ramped teeth 98 at a bottom surface 100 of thruster button 88, and cam 90 includes a plurality of ramped surfaces 102 facing upward from cam 90. The interaction of the ramped teeth 98 of thruster button 88 and the ramped surfaces 102 of cam 90 allow for longitudinal recesses 110 of cam 90 to move longitudinally downwards along internal rails 122 of housing 20 when a top portion 104 of thruster button 88 is depressed. Additionally, when cam 90 moves downward past lower shoulder 120 of internal rails 122, ramped teeth 98 of thruster button 88 interact with ramped surfaces 102 of cam 90, which causes cam 90 to rotate (e.g., counterclockwise) and lock into place in this downward position beneath lower shoulder 120. In this deployed state, a bottom portion 106 of cam 90 may contact the top surface 107 of shuttle 58 and move shuttle 58 longitudinally downwards, extending needle 40 from opening 26 in base 22 of housing 20 and into the patient's skin S. The movement of thruster button and cam 90 also compresses spring 94 beneath cam 90.

Medication delivery device 11 may sense the penetration of the skin S (e.g., by force sensors associated with thruster button 88 and/or cam 90, proximity sensors associated with shuttle 58, and/or light sensors associated with the position of syringe 35) and initiate injection of the medication 37 into the patient. As with medication delivery device 10, liquid expulsion assembly 48 (FIG. 2) may feed flexible member 74 into barrel 36 and force piston 38 towards the distal end 18 of barrel 36 thus expelling the medication 37 from needle 40 and into the patient's skin S. Flexible member 74 may be fed into barrel 36 until piston 38 has reached the bottom of barrel 36 indicating that all of the medication 37 has been delivered. The position of piston 38 can be determined either by a force sensor or stops on motor 78 of liquid expulsion assembly 48 or via proximity (e.g., light) sensor on the interior surface 30 of housing 20.

FIG. 13 shows the medication delivery device in a retracted state, once the medication 37 has been delivered to the patient, with the needle 40 retracted back into opening 26 in base 22 of housing 20. In this retracted state, the patient may depress thruster button 88 for a second time and cause cam 90 to rotate again beneath lower shoulder 120. Cam 90 may rotate to the position where longitudinal recess 110 in cam 90 realigns with internal rails 122 of housing 20. Then, cam 90 moves longitudinally upward along the rails 122 and towards the proximal end 16 of medication delivery device 11 under the force of the compressed spring 94 and retracts shuttle 58 such that needle 40 retracts into opening 26 in base 22 of housing 20.

Once medication delivery device 11 is in the retracted state, the RNS 42 may be replaced onto needle 40, and disposable portion 14 can be removed from reusable portion 12. For example, the user can replace medication delivery device 11 onto basecap 112 such that needle 40 is reinserted into RNS 42, returning to the loaded state of FIG. 8. In this loaded state, sensors associated with basecap 112 (e.g. force sensors, proximity sensors, location sensors) can determine that medication delivery device 11 has been replaced onto basecap 112 and RNS 42 has been recoupled with needle 40. As needle 40 is no longer exposed (e.g., is covered by RNS 42), it is safe for the user to remove the spent disposable portion 14 from reusable portion 12.

The user can manually remove the spent disposable portion 14 through the opening 34 in housing 20 in a similar but reverse manner as loading the disposable portion 14 into the reusable portion (e.g., sliding the carrier 44 out from the shuttle 58). The spent disposable portion 14 may be placed into a sharps container to dispose of the spent disposable portion 14. In this ejected state with the disposable portion 14 removed, the medication delivery device 11 can be placed into a sleep mode (e.g., a low power mode) and/or charged to prepare for another injection of a medication 37. The medication delivery device 11 can also send a command and/or report to the remote system indicating that the medication 37 has been delivered, including a timestamp for the delivery. The medication delivery device can then be awoken for a second time and the user can insert another disposable portion 14 though opening 34 in housing 20 for subsequent injection. The medication 37 may be the same medication 37, or may be different medication, and as discussed previously, the reusable portion 12 can accommodate different sizes of disposable portions 14.

While this invention has been shown and described as having preferred designs, the present invention may be modified within the spirit and scope of this disclosure. This application is therefore intended to cover any variations, uses or adaptations of the invention using its general principles. Further, this application is intended to cover such departures from the present disclosure as come within known or customary practice in the art to which this invention pertains.

Various aspects are described in this disclosure, which include, but are not limited to, the following aspects:

1. A medication delivery device, comprising: a disposable portion comprising: a carrier; and a syringe coupled with the carrier, the syringe comprising: a barrel containing a medication; a piston positioned within the barrel; and a needle positioned at a distal end of the barrel; a reusable portion comprising: a housing comprising a passageway extending along a longitudinal axis between a proximal end and a distal end of the housing, wherein the disposable portion is removably positioned within the passageway, and wherein the housing includes a radial opening that is configured to receive the disposable portion in a radial direction; and a shuttle comprising a guide configured to receive the carrier of the disposable portion through the radial opening; and an actuator assembly coupled with the shuttle and configured to move the disposable portion through the passageway of the housing between: a stowed state in which the needle is concealed within the distal end of the housing; a deployed state in which the needle extends from the distal end of the housing to deliver the medication to a patient; and a retracted state in which the needle is retracted into the distal end of the housing.

2. The medication delivery device of aspect 1, wherein the syringe further comprises a removeable shield, wherein the shield is decoupled from the needle in an armed state between the stowed state and the deployed state.

3. The medication device of aspect 2, wherein the housing further comprises a set of fingers extending from an interior surface of the housing, each finger coupled with a torsion spring configured to extend the finger from the interior surface of the housing and contact a top portion of the shield and decouple the shield from needle when the actuator assembly moves the disposable portion into the armed state.

4. The medication delivery device of any one of aspects 1-3, wherein the actuator assembly further comprises a linear drive component configured to move the disposable portion longitudinally in the passageway.

5. The medication delivery device of aspect 4, wherein the actuator assembly further comprises a user input in communication with the linear drive component, the user input configured to initiate extension and retraction of the linear drive component.

6. The medication delivery device of aspect 4, wherein the shuttle further comprises a drive adaptor coupled with a foot of the linear drive component, the drive adaptor comprising a tunnel configured to receive a flexible member, that extends through the tunnel and into the barrel, where the flexible member is configured to advance the piston towards the distal end of the barrel and deliver the medication from the needle.

7. The medication delivery device of aspect 6, wherein the drive adaptor further comprises a pair of channels that accept a pair of radial plungers, the radial plungers configured to extend radially outward and separate the carrier from the guide when the linear drive component moves the disposable portion towards an ejected state following the retracted state.

8. The medication delivery device of aspect 6, wherein the flexible member comprises a flexible member, the flexible member extending from a motor coupled with the housing through a hole in the housing and into the tunnel, and wherein the motor is in communication with a user input, and when the user input is engaged, the motor extends the flexible member through the hole in the housing and into the barrel to advance the piston.

9. The medication delivery device of aspect 4, wherein the passageway comprises rails extending from an interior surface about the longitudinal axis, the shuttle includes recesses to accept the rails, and the linear drive component moves the shuttle along the rails.

10. The medication delivery device of aspect 5, wherein the linear drive component comprises an electronic actuator and wherein the user input is in electrical communication with the electronic actuator and is operable to cause the electronic actuator to move axially through the housing.

11. The medication delivery device of any one of aspects 1-10, wherein the radial opening comprises a length at least long enough to receive a length of the disposable portion and a width at least wide enough to receive a width of the disposable portion.

12. The medication delivery device of any one of aspects 1-11, wherein the radial opening is uncovered.

13. The medication delivery device of any one of aspects 1-12, wherein the carrier includes a pair of horizontal protrusions, and wherein a pair of horizontal recesses in the guide accepts the pair of horizontal protrusions in a radial direction to removably couple the carrier with the guide.

14. The medication delivery device of any one of aspects 1-13, wherein the actuator assembly further comprises a lock assembly that rotates axially to unlock the medication delivery device and extends the disposable portion towards a basecap at the distal end of the housing that decouples a shield from the needle.

15. The medication delivery device of aspect 14, wherein when a user input is actuated, the actuator assembly axially rotates and advances the disposable portion towards the distal end of the housing to the deployed state.

16. The medication delivery device of aspect 15, wherein the actuator assembly is configured to retract when the user input is actuated for a second time and the disposable portion retracts towards the proximal end of the housing to the retracted state.

17. The medication delivery device of any one of aspects 1-16, wherein: the syringe is entirely visible through the radial opening of the housing in the stowed state and the retracted state; and the syringe is partially visible through the radial opening of the housing in the deployed state.

18. A method of operating a medication delivery device comprising: obtaining a disposable syringe containing a medication; inserting the disposable syringe in a radial direction through a radial opening in a reusable housing; actuating the medication delivery device to move the disposable syringe through the reusable housing in a longitudinal direction perpendicular to the radial direction and into a patient's skin and to deliver the medication into the patient's skin; retracting the disposable syringe into the reusable housing in the longitudinal direction; and removing the disposable syringe from the reusable housing.

19. The method of aspect 18, wherein: the actuating step comprises operating a motor to partially extend a linear actuator; the retracting step comprises operating the motor to retract the linear actuator; and the removing step comprises operating the motor to fully extend the linear actuator.

20. The method of any one of aspects 18-19, wherein: the removing step comprises removing the disposable syringe though the radial opening in the housing.

21. A method of delivering a medication with a medication delivery device comprising a reusable portion and a disposable portion containing the medication, the method comprising: receiving a command to activate the medication delivery device; inserting the disposable portion into a housing of the reusable portion through a radial opening in the housing wherein a carrier of the disposable portion couples with a guide of a shuttle of the reusable portion; receiving a command to remove a shield from a needle of the disposable portion, wherein the command causes an actuator to advance the guide to a first axial position within the housing where the shield contacts a set of fingers in the housing and then causes the actuator to retract the shuttle causing the shield to decouple from the needle; pressing a user input to cause the actuator to advance the guide to a second axial position within the housing to expose the needle from a distal end of the housing and deliver the medication from the disposable portion; automatically retracting the actuator to retreat the guide to a third axial position within the housing after the pressing step; receiving a command to dispose of the reusable portion, wherein the command causes the actuator to advance the guide to a fourth axial position within the housing where the guide releases the carrier.

22. The method of aspect 21, wherein the medication delivery device further comprises a motor coupled with a flexible member, and wherein when the user input is pressed, the motor extends the flexible member into a barrel of the disposable portion causing a piston within the barrel to move towards a distal end of the barrel dispensing the medication from the disposable portion.

23. The method of any one of aspects 21-22, wherein the radial opening in housing is sized to receive a second disposable portion, different from the first disposable portion, and the method further comprises: receiving a second command to activate the medication delivery device; inserting a second disposable portion into the radial opening in the housing wherein a second carrier of the second disposable portion couples with the guide of the reusable portion.

24. A method of delivering a medication with a medication delivery device comprising a reusable portion and a disposable portion containing the medication, the method comprising: Inserting the disposable portion into a housing of the reusable portion through a radial opening in the housing wherein a carrier of the disposable portion couples with a guide of a shuttle of the reusable portion; rotating a locking mechanism causing the shuttle to advance the disposable portion to a first axial position within the housing wherein a shield on a needle of the disposable portion is coupled with a basecap; separating the medication delivery device from the basecap wherein the shield is decoupled from the needle; pressing a user input for a first time causing the shuttle to advance the disposable portion to a second axial position within the housing to expose the needle from a distal end of the housing and deliver the medication; pressing the user input for a second time causing the shuttle to retract the disposable portion to a third axial position within the housing; replacing the medication delivery device on the basecap to recouple the shield and the needle; removing the disposable portion from the reusable portion in a radial direction through the opening in the housing, wherein the carrier decouples from the guide.

25. The method of aspect 24, wherein the radial opening in the housing is sized to receive a second disposable portion, different from the first disposable portion, and the method further comprises: inserting a second disposable portion into the radial opening in the housing wherein a second carrier of the second disposable portion couples with the guide of the shuttle.

26. A syringe assembly for a reusable assembly that when combined is capable of delivery of medication, comprising: a syringe comprising a barrel containing a medication, a piston positioned within the barrel, a needle positioned at a distal end of the barrel, a carrier coupled to a proximal end of the barrel, wherein the carrier includes a pair of protrusions extending radially outward and configured to be removably coupled with a linear shuttle system of a reusable assembly, and when coupled, the proximal end of the barrel is sized to receive a plunger drive of the reusable assembly, and the carrier is moved radially from the linear syringe system to decouple the carrier from the linear syringe system.

27. A reusable assembly for use with a syringe assembly that when combined is capable of delivery of medication, comprising: a housing comprising a passageway extending along a longitudinal axis between a proximal end and a distal end of the housing, and wherein the housing includes a radial opening that is configured to receive the syringe assembly in a radial direction; and a shuttle comprising a guide configured to receive a carrier of the syringe assembly through the radial opening; and an actuator assembly coupled with the shuttle and configured to move the syringe assembly through the passageway of the housing between: a deployed state in which a needle extends from the distal end of the housing to a position to expel a medication; and a retracted state in which the needle is retracted into the distal end of the housing after being in the deployed state.

28. The reusable assembly of aspect 27, wherein the actuator assembly further comprises a linear drive component configured to move the disposable portion longitudinally in the passageway.

29. The reusable assembly of aspect 28, wherein the actuator assembly further comprises a user input in communication with the linear drive component, the user input configured to initiate extension and retraction of the linear drive component.

30. The reusable assembly of any one of aspects 28-29, wherein the shuttle further comprises a drive adaptor coupled with a foot of the linear drive component.

31. The reusable assembly of aspect 30, wherein the drive adaptor comprises a tunnel configured to receive a flexible plunger member, that extends through the tunnel and into the barrel, where the flexible plunger member is configured to advance a piston of the syringe.

32. The reusable assembly of aspect 31, wherein the drive adaptor further comprises a pair of channels that accept a pair of radial plungers, the radial plungers configured to extend radially outward and separate the carrier from the guide when the linear drive component moves the disposable portion towards an ejected state following the retracted state.

33. The reusable assembly of aspect 32, wherein the flexible plunger member comprises a flexible member, the flexible member extending from a motor coupled with the housing through a hole in the housing and into the tunnel, and wherein the motor is in communication with a user input, and when the user input is engaged, the motor extends the flexible member through the hole in the housing and into the barrel to advance the piston.

34. The reusable assembly of aspect 28, wherein the passageway comprises rails extending from an interior surface about the longitudinal axis, the shuttle includes recesses to accept the rails, and the linear drive component moves the shuttle along the rails.

35. The medication delivery device of aspect 1, wherein the barrel contains the medication.

We claim:

1. A medication delivery device, comprising:

a disposable portion comprising:

a carrier; and a syringe coupled with the carrier, the syringe comprising:

a barrel to contain a medication;

a piston positioned within the barrel; and a needle positioned at a distal end of the barrel;

a reusable portion comprising:

a housing comprising a passageway extending along a longitudinal axis between a proximal end and a distal end of the housing, wherein the disposable portion is removably positioned within the passageway, and wherein the housing includes a radial opening that is configured to receive the disposable portion in a radial direction; and a shuttle comprising a guide configured to receive the carrier of the disposable portion through the radial opening;

a flexible plunger member configured to bend and extend through the guide, wherein the flexible plunger member comprises a metal wire, a polymer ribbon, a rubber ribbon, a polymer coil, or metal coil; and an actuator assembly coupled with the shuttle and configured to move the disposable portion through the passageway of the housing between:

a stowed state in which the needle is concealed within the distal end of the housing;

a deployed state in which the needle extends from the distal end of the housing to deliver the medication to a patient; and a retracted state in which the needle is retracted into the distal end of the housing, wherein, while in the deployed state, the flexible plunger member is configured to advance the piston within the barrel.

2. The medication delivery device of claim 1, wherein the syringe further comprises a removeable shield, wherein the shield is decoupled from the needle in an armed state between the stowed state and the deployed state.

3. The medication device of claim 2, wherein the housing further comprises a set of fingers extending from an interior surface of the housing, each finger coupled with a torsion spring configured to extend the finger from the interior surface of the housing and contact a top portion of the shield and decouple the shield from needle when the actuator assembly moves the disposable portion into the armed state.

4. The medication delivery device of claim 1, wherein the actuator assembly further comprises a linear drive component configured to move the disposable portion longitudinally in the passageway.

5. The medication delivery device of claim 4, wherein the actuator assembly further comprises a user input in communication with the linear drive component, the user input configured to initiate extension and retraction of the linear drive component.

6. The medication delivery device of claim 5, wherein the linear drive component comprises an electronic actuator and wherein the user input is in electrical communication with the electronic actuator and is operable to cause the electronic actuator to move axially through the housing.

7. The medication delivery device of claim 4, wherein the shuttle further comprises a drive adaptor coupled with a foot of the linear drive component, the drive adaptor comprising a tunnel configured to receive the flexible plunger member, that extends through the tunnel and into the barrel, where the flexible plunger member is configured to advance the piston towards the distal end of the barrel and deliver the medication from the needle.

8. The medication delivery device of claim 7, wherein the drive adaptor further comprises a pair of channels that accept a pair of radial plungers, the radial plungers configured to extend radially outward and separate the carrier from the guide when the linear drive component moves the disposable portion towards an ejected state following the retracted state.

9. The medication delivery device of claim 7, wherein the flexible plunger member is extended from a motor coupled with the housing through a hole in the housing and into the tunnel, and wherein the motor is in communication with a user input, and when the user input is engaged, the motor extends the flexible plunger member through the hole in the housing and into the barrel to advance the piston.

10. The medication delivery device of claim 4, wherein the passageway comprises rails extending from an interior surface about the longitudinal axis, the shuttle includes recesses to accept the rails, and the linear drive component moves the shuttle along the rails.

11. The medication delivery device of claim 1, wherein the radial opening comprises a length at least long enough to receive a length of the disposable portion and a width at least wide enough to receive a width of the disposable portion.

12. The medication delivery device of claim 1, wherein the radial opening is uncovered.

13. The medication delivery device of claim 1, wherein the carrier includes a pair of horizontal protrusions, and wherein a pair of horizontal recesses in the guide accepts the pair of horizontal protrusions in a radial direction to removably couple the carrier with the guide.

14. The medication delivery device of claim 1, wherein the actuator assembly further comprises a lock assembly that rotates axially to unlock the medication delivery device and extends the disposable portion towards a basecap at the distal end of the housing that decouples a shield from the needle.

15. The medication delivery device of claim 14, wherein when a user input is actuated, the actuator assembly axially rotates and advances the disposable portion towards the distal end of the housing to the deployed state.

16. The medication delivery device of claim 15, wherein the actuator assembly is configured to retract when the user input is actuated for a second time and the disposable portion retracts towards the proximal end of the housing to the retracted state.

17. The medication delivery device of claim 1, wherein:

the syringe is entirely visible through the radial opening of the housing in the stowed state and the retracted state; and the syringe is partially visible through the radial opening of the housing in the deployed state.

18. The medication delivery device of claim 1, wherein the barrel contains the medication.

19. A reusable assembly for use with a syringe assembly that when combined is capable of delivery of medication, the syringe assembly comprising a barrel and a piston, the assembly comprising:

a housing comprising a passageway extending along a longitudinal axis between a proximal end and a distal end of the housing, and wherein the housing includes a radial opening that is configured to receive the syringe assembly in a radial direction; and a shuttle comprising a guide configured to receive a carrier of the syringe assembly through the radial opening; and an actuator assembly coupled with the shuttle and configured to move the syringe assembly through the passageway of the housing between:

a deployed state in which a needle extends from the distal end of the housing to a position to expel a medication; and a retracted state in which the needle is retracted into the distal end of the housing after being in the deployed state, wherein the actuator assembly comprises a flexible plunger member that extends through a portion of the shuttle and distally into the barrel of said syringe assembly to advance the piston, wherein the flexible plunger member comprises a metal wire, a polymer ribbon, a rubber ribbon, a polymer coil, or metal coil.

20. The reusable assembly of claim 19, wherein the actuator assembly further comprises a linear drive component configured to move the disposable portion longitudinally in the passageway.

21. The reusable assembly of claim 20, wherein the actuator assembly further comprises a user input in communication with the linear drive component, the user input configured to initiate extension and retraction of the linear drive component.

22. The reusable assembly of claim 20, wherein the shuttle further comprises a drive adaptor coupled with a foot of the linear drive component.

23. The reusable assembly of claim 22, wherein the drive adaptor further comprises a pair of channels that accept a pair of radial plungers, the radial plungers configured to extend radially outward and separate the carrier from the guide when the linear drive component moves the disposable portion towards an ejected state following the retracted state.

24. The reusable assembly of claim 22, wherein the flexible plunger member extends from a motor coupled with the housing through a hole in the housing and into a tunnel formed in the drive adaptor, and wherein the motor is in communication with a user input, and when the user input is engaged, the motor extends the flexible plunger member through the hole in the housing and into the barrel to advance the piston.

25. The reusable assembly of claim 20, wherein the passageway comprises rails extending from an interior surface about the longitudinal axis, the shuttle includes recesses to accept the rails, and the linear drive component moves the shuttle along the rails.

26. A medication delivery device, comprising:

a disposable portion comprising a syringe, the syringe comprising a barrel to contain a medication, a piston positioned within the barrel, and a needle positioned at a distal end of the barrel; and a reusable portion comprising a housing comprising a passageway extending along a longitudinal axis between a proximal end and a distal end of the housing, wherein the disposable portion is positioned within the passageway, and a shuttle configured to receive a portion of the disposable portion, a flexible plunger member configured to bend and extend through the shuttle, wherein the flexible plunger member comprises a metal wire, a polymer ribbon, a rubber ribbon, a polymer coil, or metal coil, and an actuator assembly coupled with the shuttle and configured to move the disposable portion through the passageway of the housing between a stowed state in which the needle is concealed within the distal end of the housing, a deployed state in which the needle extends from the distal end of the housing to deliver the medication to a patient, and a retracted state in which the needle is retracted into the distal end of the housing, wherein, while in the deployed state, the flexible plunger member is configured to advance the piston within the barrel, and, after the deployed state, the flexible plunger member is configured to be retracted from the barrel.

* * * * *